United States Patent [19]

Cham et al.

[11] Patent Number: 5,958,770

[45] Date of Patent: *Sep. 28, 1999

[54] GLYCOALKALOIDS

[76] Inventors: Bill Elliot Cham, 772 Upper Brookfield Rd., Upper Brookfield, Queensland, 4069; Brian Daunter, 2 Mazzard St., Bellbowrie, Queensland, 4067, both of Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/743,671

[22] Filed: Nov. 6, 1996

Related U.S. Application Data

[63] Continuation of application No. 07/916,880, filed as application No. PCT/AU91/00020, Jan. 18, 1991, abandoned.

[30] Foreign Application Priority Data

Jan. 18, 1990 [AU] Australia ................................ PJ 8243

[51] Int. Cl.$^6$ .................................................. A61K 31/705
[52] U.S. Cl. .................................. 435/375; 424/DIG. 14; 514/26; 514/27; 514/841; 514/843
[58] Field of Search .................................... 435/7.2, 7.21, 435/29, 375; 436/827; 514/27–28, 841, 843; 424/DIG. 14

[56] References Cited

U.S. PATENT DOCUMENTS

| | | | |
|---|---|---|---|
| 4,937,182 | 6/1990 | Hancock et al. | 435/29 |
| 5,227,160 | 7/1993 | Nudelman et al. | 514/843 |
| 5,766,632 | 6/1998 | Oldham et al. | 514/841 |

FOREIGN PATENT DOCUMENTS

| | | |
|---|---|---|
| 74958/87 | 1/1988 | Australia . |
| 1 151 549 | 8/1983 | Canada . |
| 943 800 | 3/1949 | France . |
| 1 804 331 | 5/1969 | Germany . |
| 1 900 060 | 8/1970 | Germany . |
| 25 19 261 | 11/1976 | Germany . |
| 1 380 253 | 1/1975 | United Kingdom . |

OTHER PUBLICATIONS

W. J. Herbert et al (EDS.), *Dictionary of Immunology*, Third Edition, Blackwell Scientific Publications, 1985, p. 6.

H. A. Sober et al, *CRC Handbook of Biochemistry*, The Chemical Rubber Co., 1968, p. D–26.

M. Monsignt et al, Ann. N.Y. Acad. Sci., 551, 399–414, 1988.

Martinez et al., "Chapter 37, Immunotoxins", Handbook of Experimental Immunology, vol. 1, Immunochemistry 1986.

"The Merck Index", pp. 520, 1371–1372, 1487, Eleventh Edition, 1989.

Fieser et al., "Steroids", pp. 819, 848, 777 (1959).

Heftmann et al., "Biochemistry of Steroids", pp. 48 and 55 (1960).

Arai et al., "Cytokines: Coordinators of Immune and Inflammatory Responses", pp. 783–835, Annu. Rev. Biochem., vol. 59 (1990).

Derwent Abstract Accession No. 35682D/20, Class B01, SU–724–521.

Derwent Soviet Inventions Illustrated, Nov. 1972, Pharmaceuticals, Photographic p. 7, SU–336023, 24 May 1972.

Patent Abstracts of Japan, JP–A–60–1130, p. 73, 7 Jan. 1985.

Derwent Abstract Ascension No. 90–338476/45, Class B01, JP–A–2243631, 27 Sep. 1990.

Cham et al., "Glycoalkaloids From Solanum Sodomaeum Are Effective In The Treatment Of The Skin Cancers In Man", Cancer Letters 36 (1987), pp. 111–118.

Cham et al., "Antitumour Effects Of Glycoalkaloids Isolated From Solanum Sodomaeum", Planta Medica 1987, pp. 34–36.

Cham et al., "HPLC Of Glycoalkaloids from Solanum Sodomaeum", Planta Medica 1987, pp. 59–62.

Cham, B.E., "BEC", Drugs of the Future, vol. 13, No. 8, 1988, pp. 714–716.

Cham et al., "Curaderm (Antineoplastic) Launched In Australia", Drug News & Perspectives 2(2), Mar. 1989, p. 112.

"Plants Yield Skin Cancer Cure", Australian Technology Review 1988, p. 53.

*Primary Examiner*—David Saunders
*Attorney, Agent, or Firm*—Larson & Taylor

[57] ABSTRACT

The invention is directed to the control of cellular autophagy, cellular agglutination and the immobilization of motile cells. Such control is useful in, for example, the treatment of cancer, contraception, termination of pregnancy, removal of pathogenic organisms and removal of any abnormal cellular growth (malignant or otherwise); as a diagnostic and analytical tool whereby cell structure can be studied and testing could be undertaken for the presence (and subsequent analysis) of pathogenic and non-pathogenic organisms; and in the manufacture of biochemicals whereby certain cells must be destroyed or otherwise contained. From surface analysis of normal and abnormal cells, specific receptors on abnormal cells which are either not present on normal cells or are only present in significantly reduced numbers can be identified. Alkaloids and other pharmaceutically acceptable compounds are preferentially recognized by the abnormal cells, and which bind thereto and subsequently destroy.

6 Claims, 11 Drawing Sheets a = OVARIAN CANCER CELL LINE
b = HELA CELLS
c = LYMPHOBLASTOID
d = FIBROBLASTS

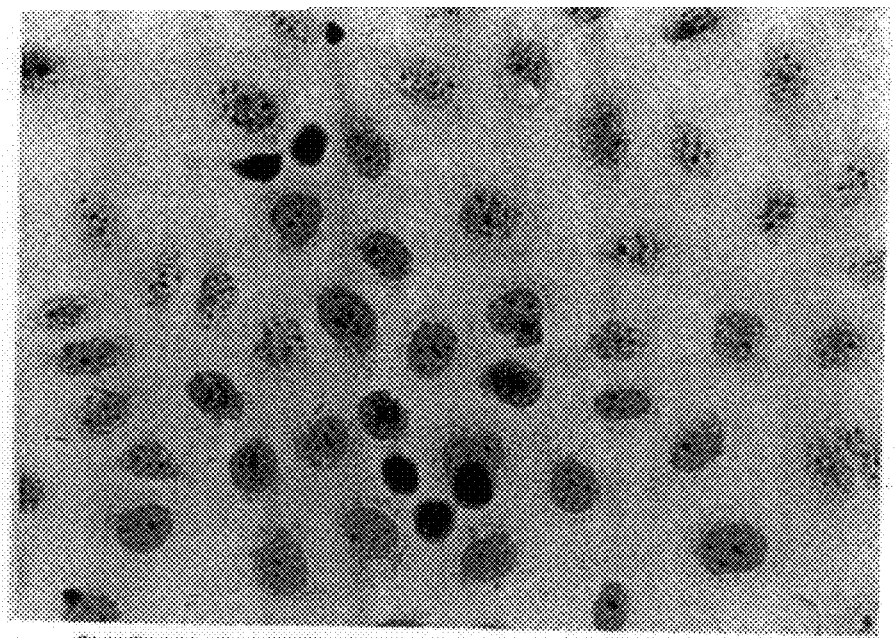
OVARIAN CANCER CELLS IN THE PRESENCE OF THE
AGLYCONE SOLASODINE 96.8 μM/L 3 HOURS
Fig.2A. (×1000)
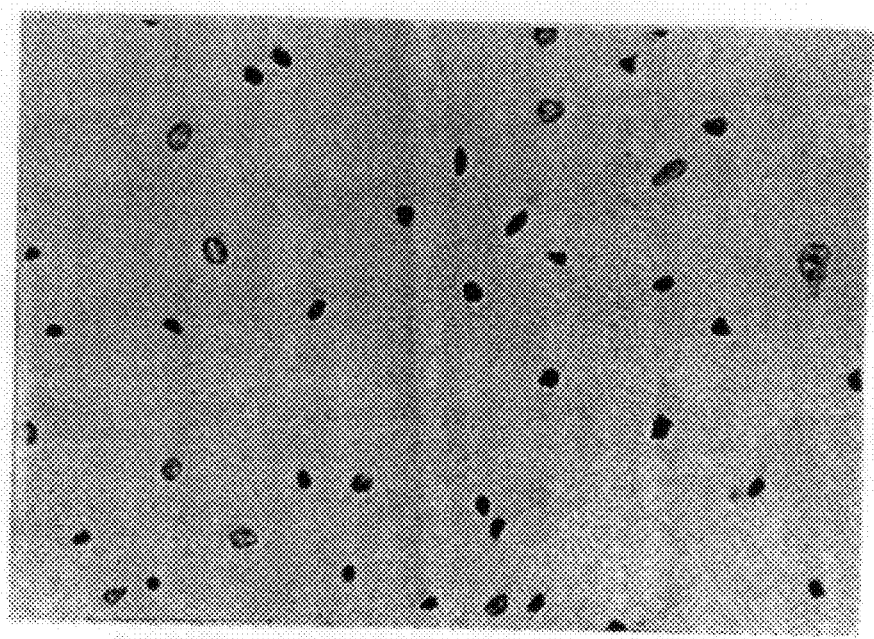
OVARIAN CANCER CELLS IN THE PRESENCE OF
SOLASODINE GLYCOSIDES EXPRESSED IN TERMS
OF SOLAMARGINE 6.1 μM/L 3 HOURS
Fig.2B. (×1000)

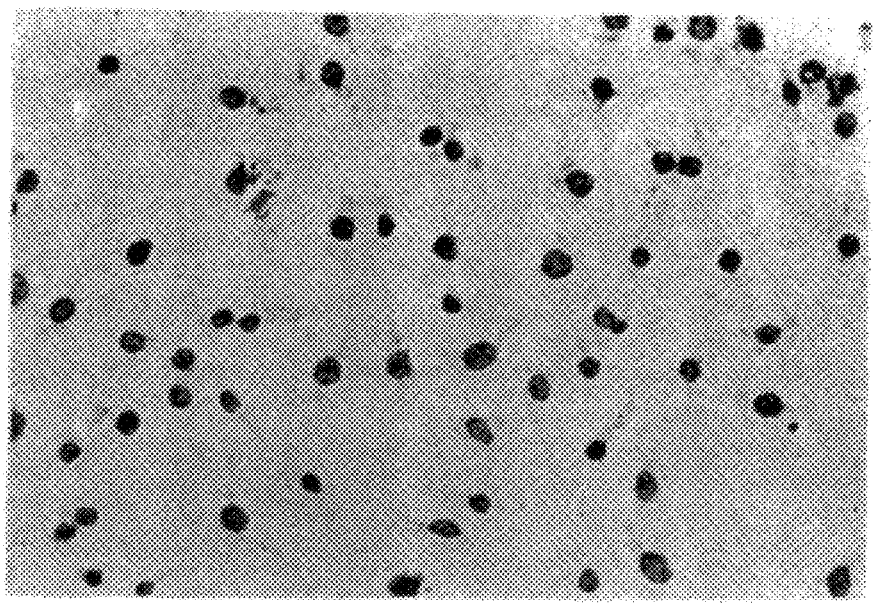
OVARIAN CANCER CELLS IN THE PRESENCE OF SOLASODINE GLYCOSIDES EXPRESSED IN TERMS OF SOLAMARGINE 9·6 µM/L 3 HOURS
Fig.3A.   (×1000)
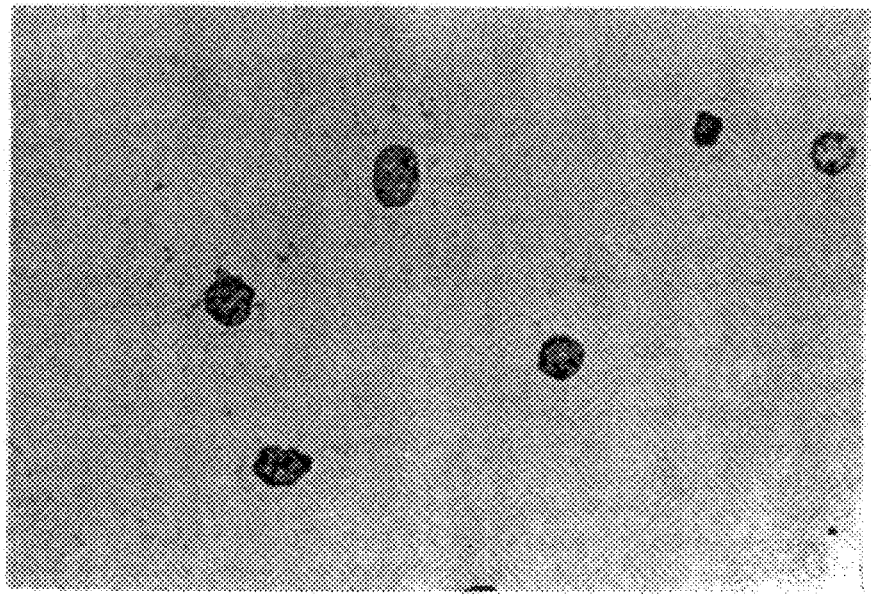
OVARIAN CANCER CELLS IN THE PRESENCE OF SOLASODINE GLYCOSIDES EXPRESSED IN TERMS OF SOLAMARGINE 11·1 µM/L 3 HOURS
Fig.3B.   (×1575)

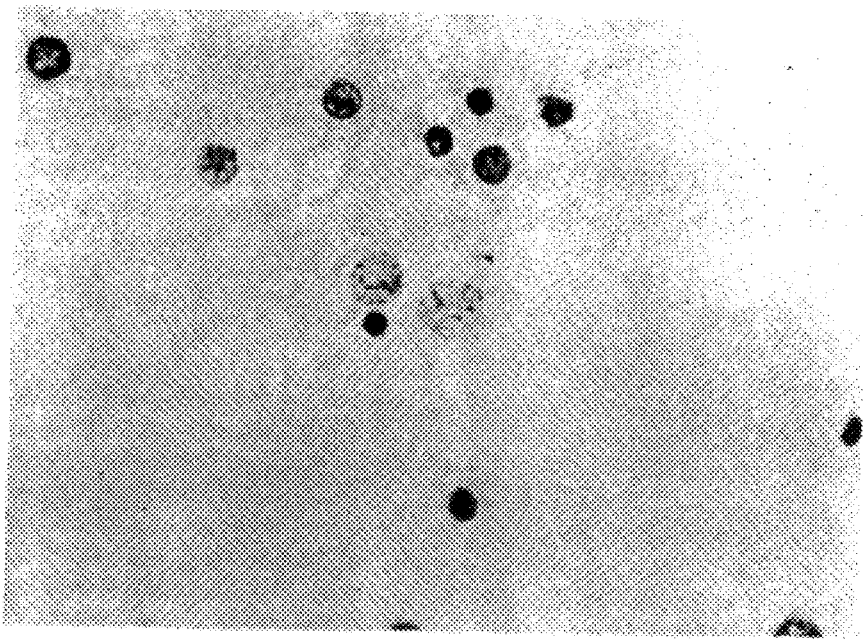
OVARIAN CANCER CELLS IN THE PRESENCE OF SOLASODINE GLYCOSIDES
EXPRESSED IN TERMS OF SOLAMARGINE 15·3 μM/L 3 HOURS
Fig.4A. (×1575)
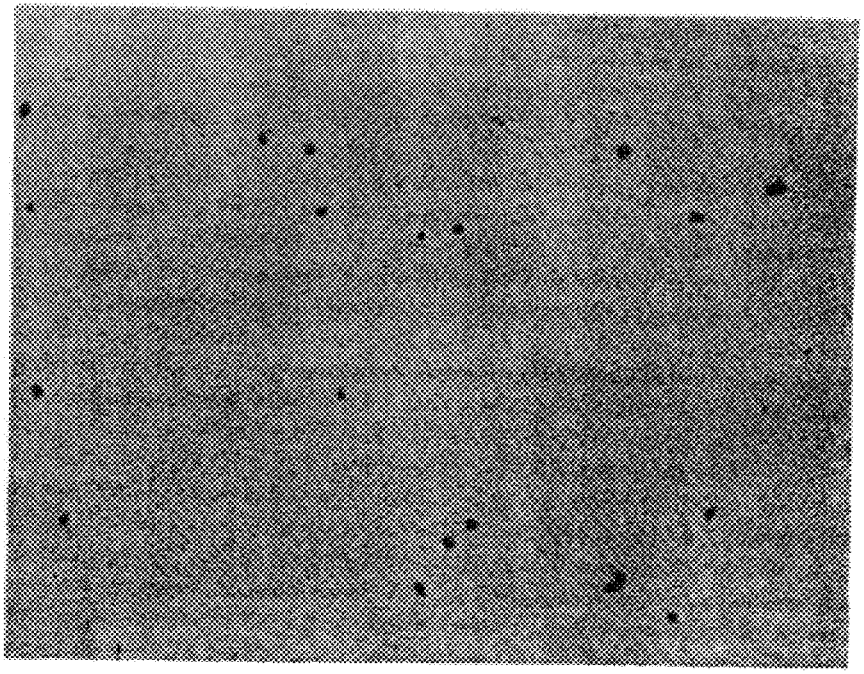
OVARIAN CANCER CELLS IN THE PRESENCE OF SOLASODINE GLYCOSIDES
EXPRESSED IN TERMS OF SOLAMARGINE 3·1 μM/L 17 HOURS
Fig.4B.

DEAD INTACT SPERMATOZOA IN THE ZONE OF SOLAMARGINE/EOSIN

GLYCOALKALOIDS

CROSS-REFERENCE TO RELATED APPLICATIONS

This application is a continuation of application Ser. No. 07/916,880 filed May 27, 1994 and now abandoned, which was filed under 35 USC 371 claiming benefit of PCT/AU91/00020 filed Jan. 18, 1991.

TECHNICAL FIELD

THIS INVENTION is directed to cellular autophagy. In particular, it is directed to the control of cellular autophagy, cellular agglutination and the immobilization of motile cells.

BACKGROUND ART

Controlled autophagy and/or agglutination or immobilization of cells should be very useful for a wide variety of therapeutic and other medical and non-medical uses.

Before describing the present invention in detail, it is first important to appreciate the differences between autophagy, cell lysis and apoptosis.

Autophagy (or self digestion) is the result of disrupting the cellular organelle—the lysosome—directly or indirectly, for example, by inhibition of mitochondrial activity. The cell thus digests itself from the inside, including digesting the plasma membrane of the cell, to leave behind the nucleus that is also partly digested and fragments.

Cell lysis, however, is cell death due to leakage of material from the cell and can be induced by changing the osmotic strength of the media surrounding the cell. Cell lysis can be induced by causing damage to the plasma membrane of the cell, for example with enzymes or antibiotics, to induce osmotic shock. Also in haemolysis, which is the specific lysis of red blood cells, haemoglobin is extruded by the cell to leave behind a damaged red blood cell membrane.

Finally, apoptosis is the fragmentation of the nucleus and the encapsulation of these fragments and cell organelles in plasma membrane fragments—this does not involve cell lysis or autophagy.

Traditional treatment for an infected host is the destruction of the invading virus or the like, leaving the cells of the host intact. Similarly, if abnormal cell growth of the host is responsible for the malady, then treatment, obviously, must only target the abnormal cells, leaving the normal cells intact.

Treatment of the latter type of malady, eg cancer and related diseases, has been the subject of much research and a large range of chemical compounds have been investigated with mixed results.

Preference for treatment with naturally occurring compounds is increasing and of the many alkaloids currently used or tested in medicine, many have been extracted from plants. In particular, the use of extracts of the plant species Solanum as an effective treatment of certain cancers has been known since at least 1825. Research into these extracts from 1965 onwards has established that the antineoplastic compound(s) was most likely a glycoalkaloid(s). Examples include B-solamarine, a glycoalkaloid extracted from *Solanum dulcamara* as a tumour inhibitor, and other glycoalkaloids extracted from *Solanum sodomaeum L.* which possess antineoplastic activity both in mice and humans. Another example is Solaplumbin—which is rhamnosyl [4→3] Solasodine—obtained from *Nicotiana plumbaginifolia* which has been shown to have anticancer properties in rats.

However, specificity remains a problem and it is not always possible to target solely the invading virus or the like or to only affect abnormal cells of the host.

DISCLOSURE OF THE INVENTION

The present inventors' studies of normal and abnormal cells have discovered specific receptors on abnormal cells which are either not present on normal cells or are only present in significantly reduced numbers such that certain compounds are preferentially recognised by the abnormal cells, and which bind thereto and subsequently destroy. Once these receptors have been identified it has also been discovered that certain alkaloids and other pharmaceutically acceptable compounds can be used to control cellular autophagy, cellular agglutination and immobilization of motile cells.

With such control, it would be far easier to target a particular cell for destruction or some other modification and would be useful in, for example, the treatment of cancer, contraception, termination of pregnancy, removal of pathogenic organisms and removal of any abnormal cellular growth (malignant or otherwise). It would also be useful as a diagnostic and analytical tool whereby cell structure could be studied and testing could be undertaken for the presence (and subsequent analysis) of pathogenic and non-pathogenic organisms. This control of cellular function would also be useful in the manufacture of biochemicals whereby certain cells must be destroyed or otherwise contained.

The present inventors have discovered that, by identifying a particular receptor site of the target cell and coupling a suitable compound thereto, the required control of cellular function can be achieved.

Thus, according to one aspect of the present invention, there is provided a method for identifying a compound suitable to control cell autophagy, cell agglutination or immobilization of motile cells, said method comprising:

(a) analyzing the surface of each of a target cell and of a non-target cell;

(b) identifying receptor sites on said surface of said target cell which are either not present or only present in significantly reduced numbers on said surface of said non-target cell; and (c) selecting a compound which will selectively bind to said receptor sites of said target cell and which will exert said control.

As a second aspect of the present invention, there is provided a method to control cell autophagy, cell agglutination or immobilization of motile cells, said method comprising:

(a) identifying a compound suitable for the required control by the method as hereinbefore defined; and (b) binding said compound to said receptor sites of said target cell.

A third aspect of the present invention is the provision of a compound which is suitable for the control of cell autophagy, cell agglutination or immobilization of motile cells by the method as hereinbefore defined.

Preferably, the control of cellular function by the present invention is by using compounds of the general formula (1):

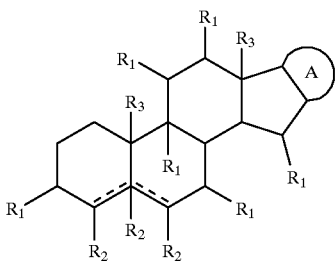

wherein:
either one of the dotted lines represents a double bond, and the other a single bond, or both represent single bonds;
"A" represents a radical selected from the following radicals of general formulae (II) to (V):

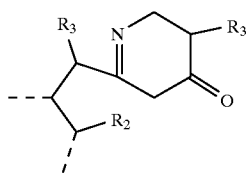

(II)

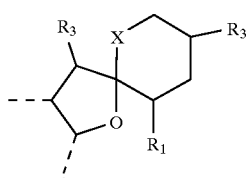

(III)

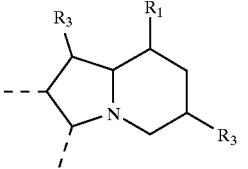

(IV)

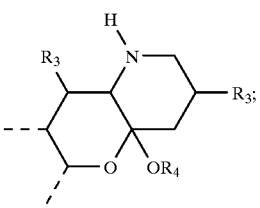

(V)

each of $R^1$ is a radical separately selected from the group comprising hydrogen, amino, oxo and $OR^4$;
each of $R^2$ is a radical separately selected from the group comprising hydrogen, amino and $OR^4$;
each of $R^3$ is a radical separately selected from the group comprising hydrogen, alkyl and $R^4O$-alkylene;
each of $R^4$ is a radical separately selected from the group comprising hydrogen, carbohydrate and a carbohydrate derivative;
"X" is a radical selected from the group comprising —$CH_2$—, —O— and —NH—.

For non-carbohydrate compounds of general formula (1), the preferred compounds are solasodine, solanidine, diosgenin, solangustidine, leptinidine, solacongestidine, solafloridine, demissidine, soladulcidine, tomatidenol, paniculidine, jurjubidine, tigogenin, yamogenin and neotigogenin.

The more preferred compounds are solasodine and solanidine.

When the compounds of general formula (1) represent a carbohydrate (such as a mono, oligo or polysaccharide) or a derivative thereof, the preferred radicals $R^4$ are glyceric aldehyde; glycerose; erythrose; threose; ribose; arabinose; xylose; lyxose; altrose; allose; gulose; mannose; glucose; idose; galactose; talose; rhamnose; dihydroxyacetone; erythrulose; ribulose; xylulose; psicose; fructose; sorbose; tagatose; and other hexoses ($C_6H_{12}O_6$); heptoses ($C_7H_{14}O_7$); octoses ($C_8H_{16}O_8$); nanoses ($C_9H_{18}O_9$); decoses ($C_{10}H_{20}O_{10}$); deoxysugars with branched chains (eg apiose, hamamelose, streptose, cordycepose, mycarose and cladinose); compounds wherein the aldehyde, ketone or hydroxyl groups have been substituted (eg N-acetyl, acetyl, methyl, replacement of $CH_2OH$); sugar alcohols; sugar acids; benzimidazoles; the enol salts of the carbohydrates; saccharinic acids; sugar phosphates.

The more preferred compounds are solasonine, solamargine and solanine.

Other preferred compounds of the general formula (1) are solanocapsine and 26-aminofurostane.

It will be appreciated that the various compounds referred to throughout this specification may be chiral and the present invention relates both to the individual stereoisomers and to any mixtures thereof including mixtures of enantiomers and/or diastereoisomers.

Although not wishing to be bound by theory, the proposed mechanism of autophagy induction by the preferred compounds of the present invention wherein all of the radicals $R^1$ represent hydrogen is by diffusion through the plasma membrane of the cell to interact either directly with the lysosome causing its disruption or/and indirectly by inhibition of mitochondrial activity. When $R^1$ is other than hydrogen, the mechanism of entry into the cell is by receptor mediated endocytosis. In the case of $R^1$ representing carbohydrate (ligand), the receptors are endogenous lectins.

This receptor mediated endocytosis is important because, as different cells express different receptors for various compounds, it is thus possible to couple any ligand (which interacts with a specific cell-surface receptor) to specifically induce autophagy and/or cell agglutination or immobilization of different cell types.

Suitable ligands other than carbohydrates include the steroid and non-steroid hormones, (eg, progesterone, insulin, oestrogen, growth hormone), growth factors, polyamines, cytokines, lymphokines, lymphotoxins, chalones, fatty acids and cholesterol—ie, essentially any chemical messenger required for endocytosis.

Once such a ligand has been identified and coupled to the appropriate steroid derivative or other compound, administration to the cell-containing host should induce cell autophagy and/or cell agglutination or immobilization.

It should be noted that it is not essential that the aforesaid ligand be directly coupled to the said steroid or other compound. For example, the said steroid or other compound could be attached to one end of a suitable organic or inorganic carrier, such as a polymer, with the ligand coupled to the other end of the carrier. This indirect coupling of the ligand to the steroid or the like could provide a convenient delivery system for the present invention when it is inappropriate, for whatever reason, to directly couple the ligand to the active component.

This ability to control cellular function at will is not evident from the current prior art. Different diseases require different treatment—a treatment effective against skin cancer is unlikely to be as effective against, for example, ovarian cancer as the malignant cells have different receptors. For example, although it is known that certain glycosides are effective against certain cancers, these same glycosides have not been assessed for their potential use against other cancers nor has their mode of action been studied. It is believed that the present inventors are the first to have studied this mode of action, identified those receptor sites on "abnormal" cells which differ from those on "normal" cells and by a suitable selection of an appropriate compound, achieved a required control on cellular function.

For their use in practice, the compounds of the present invention are not generally employed by themselves. Preferably, they are used in a composition containing one or more of the compounds, in association with any pharmaceutical-type carrier or diluent which is suitable for its administration.

As used throughout the specification, the term "carrier of diluent" denotes an organic or inorganic, natural or synthetic material with which the active ingredient is combined in order to facilitate the administration of the invention. This carrier or diluent is, therefore, generally inert and it must be pharmaceutically acceptable.

With the cellular control available from the present invention, it should be possible to target a particular cell for destruction or modification necessary in, for example, the treatment of cancer, contraception, termination of pregnancy, removal of pathogenic organisms and removal of abnormal cellular growth.

Thus, as a fourth aspect of the present invention, there is provided a method of inducing cell autophagy, cell agglutination or immobilization within an animal body (including humans), said method comprising administering to said animal a compound or a composition, both as hereinbefore defined.

The present invention should also be useful as a diagnostic and analytical tool whereby a compound found to selectively bind to a target cell could be initially further modified to enable its detection by suitably available techniques, thus acting as a "marker" identifying the target cell.

Thus, according to a fifth aspect of the present invention, there is provided a method of marking and identifying a target cell said method comprising:

(a) identifying a compound suitable to control cell autophagy, cell agglutination or immobilization of motile cells by the method as hereinbefore defined;

(b) further modifying said compound to enable detection of the thus modified compound;

(c) inducing cell autophagy, cell agglutination or cell immobilization by the method as hereinbefore defined; and (d) detecting said modified compound by any appropriate means.

Preferably, said compound is modified by further conjugation with another compound, this other compound being detectable by its fluorescence or radioactivity.

For example, a compound of the general formula (1) as hereinbefore defined could be reacted with the fluorescent reagent dansyl chloride, or said compound could be modified to incorporate the usual radiolabel(s) known in the art. The thus modified compound could be purified before its use in the induction of cell autophagy, agglutination or immobilization and the progress of the binding followed under a fluorescence microscope or radioactivity counter as applicable. If the binding is undertaken at a low temperature, the internalization of the marked compound will be slow allowing the binding to be followed.

BRIEF DESCRIPTION OF THE DRAWINGS

FIG. 2A is a microscopic photograph of ovarian cancer cells in the presence of the aglycone solasodine (96.8 $\mu$M/L, 3 hours).

FIG. 2B is a microscopic photograph of ovarian cancer cells in the presence of solasodine glycosides expressed in terms of solamargine (6.1 $\mu$M/L, 3 hours).

FIG. 3A is a microscopic photograph of ovarian cancer cells in the presence of solasodine glycosides expressed in terms of solamargine (9.6 $\mu$M/L, 3 hours).

FIG. 3B is a microscopic photograph of ovarian cancer cells in the presence of solasodine glycosides expressed in terms of solamargine (11.1 $\mu$M/L, 3 hours).

FIG. 4A is a microscopic photograph of ovarian cancer cells in the presence of solasodine glycosides expressed in terms of solamargine (15.3 $\mu$M/L, 3 hours).

FIG. 4B is a microscopic photograph of ovarian cancer cells in the presence of solasodine glycosides expressed in terms of solamargine (3.1 $\mu$M/L, 17 hours).

DETAILED DESCRIPTION OF EMBODIMENTS

Figure 1A:
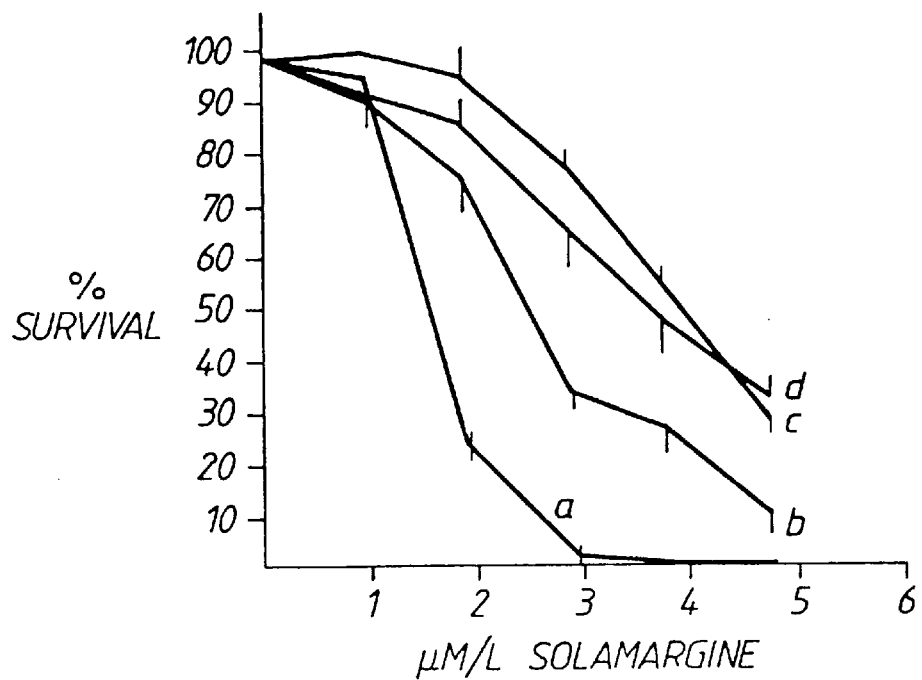
FIGS. 1a, 1b, 1c, and 1d, respectively, are dose response curves showing the lethal dose (LD) of cytotoxics required to inhibit 50% ($LD_{50}$) uptake of tritiated thymidine.
Figure 1B:
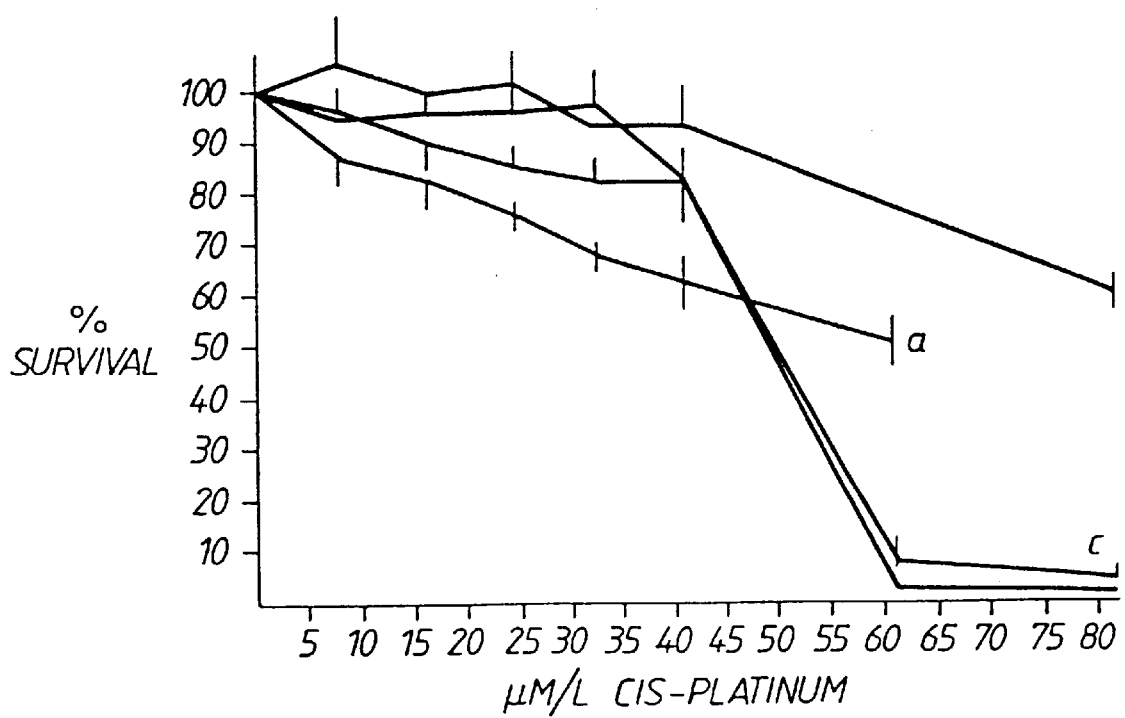

Specific details of the compounds and methods of the present invention will now be illustrated. The technical terms identified have the usual meaning in the art.

General

Solasodine glycosides can be isolated and purified as a mixture (known as BEC) comprising solamargine (33%), solasonine (33%) together with di- and mono-glycosides (34%) or as separate components (Cura Nominees Pty Ltd, Australia) and these compounds have been investigated for the inhibition of cell replication of human cells, ovarian cancer cells, melanoma cells, cells infected with viruses, normal fibroblasts, normal bone marrow cells, leukemic cells and normal lymphocytes. The inhibition of the glycosides of solasodine have been demonstrated with the appropriate "free" sugars and covalently bound to bovine serum albumin. The sugars that have been investigated and shown to have inhibitory effects on the action of the mixture of solasodine glycosides are as follows: glucose $\alpha$ and $\beta$, NAc glucosamine NAc glucose, mannose $\alpha$ and $\beta$, NAc mannosamine NAc mannose, galactose $\alpha$ and $\beta$ and the disaccharide lactose.

Chlorambucil (Sigma Chemical Co., USA), 1–2 mg was dissolved in 50 µl of DMSO and diluted immediately before use in TCM+10% FCS. Cis-platinum was supplied as a saline solution (David Bull Laboratories, Australia), and was diluted with TCM+10% FCS. Vinblastine (Sigma Chemical Co., USA) was dissolved in TCM+10% FCS. Solasodine glycosides, 100 mg were dissolved in 5 ml DMSO and diluted with TCM+10% FCS to give a 5% solution of DMSO, and further diluted before use. Appropriate DMSO cytotoxicity studies were also conducted.

Peripheral blood human lymphocytes were isolated using an Isopaque-Ficoll gradient and cultured in replicates of 10 in microwell titre plates. $2\times10^5$ lymphocytes/well ($1\times10^6$/ml) in $CO_2$ 1640 tissue culture media supplemented with 10% fetal calf serum containing 20 µg/ml of photohaemagglutinin (PHA), concanavalin A (Con A) or pokeweed nitrogen (PWM). This was cultured for 48 hours and pulsed with tritiated thymidine for a further 24 hours. In the inhibition studies, the cell concentration was $8\times10^5$/ml.

In Vitro Preferential Cytotoxicity for Human Cancer Cells

The inhibition of cell replication by steroid alkaloids is determined by the inhibition of the incorporation of $^3H$ thymidine into DNA. Using this technique, it should be possible to monitor any preferential inhibition of uptake of $^3H$ thymidine by cancer cells.

Below it is shown that solamargine, a glycoside of solasodine, preferentially inhibits the uptake of tritiated thymidine by cancer cells. In contrast, solamargine at equivalent concentration, and the mono- and di-glycosides of solasodine had a limited effect on the uptake of tritiated thymidine for other cell types, including unstimulated lymphocytes and lymphocytes stimulated with Con A. Also, the solasodine glycosides do not inhibit the uptake of tritiated thymidine by lymphocytes stimulated with PHA or PWM. The inhibition of tritiated thymidine uptake by solamargine and the mono- and di-glycosides of solasodine are dependent upon their cellular uptake by endogenous endocytic lectins (EELs). The mode of action of the solasodine glycosides, in particular solamargine, appears to be the induction of cell lysis, as determined by morphological examination.

Cells were maintained as monolayers in RPM1-1640 tissue culture media (Grant Island Biological Co) buffered with N-2-hydroxy-ethylpiperazine-N-2-ethanesulphonic acid pH 7.5 and supplemented with 10% heat inactivated fetal calf serum (FCS): (i) a human ovarian cancer cell line (C180–135), (ii) HeLa cells, (iii) human fibroblasts, and (iv) as a cell suspension of lymphoblastoid cells (EBV transformed lymphocytes). Monolayers were trypsinized to form a cell suspension. All cell suspensions were passed through a 21 gauge syringe needle to remove cell clumps (95% viability). Cell concentration was adjusted to $2\times10^5$ cells/ml, and $2\times10^4$ cells were added in replicates of 10 to the wells ($1\times10^5$/ml well) of HA microtitre plates (Millipore Corp., USA). The cells were preincubated at 37.5° C. for 7 hours prior to the addition of 50 µl of the cytotoxic drug followed by the addition of 50 µl 5 uCi/ml of $^3H$ thymidine, in the same tissue culture media 21 hours later. Incubation was continued for a total of 24 hours, which includes the pre-incubation time.

All cells were harvested by vacuum filtration by washing in 250 µl of each of phosphate buffered saline, 5% trichloroacetic acid, 1.0M NaCl and 95% ethanol and subjected to β-scintillatian counting. Similarly, peripheral human blood lymphocytes were isolated and cultured $2\times10^5$ lymphocytes in $CO_2$ 1640TCM 10% HIFCS. Lymphocytes were stimulated with 20 µg/ml PHA, Con A or PWM, and cultured for 48 hrs followed by a 24 hr pulse. Inhibition of cytotoxicity was carried out with lactose, lactosyl-albumin, glucose, galactose or rhamnase (Sigma Chemical Co., USA). Cell concentrations were $8\times10^4$/well total volume 250 µl. The dpm of the experimental replicates were expressed as a percentage of the mean value of the controls, and the mean value of the experimental replicates calculated. The SD of the controls did not exceed 10% of their mean value.

Cytotoxic drugs studied included chlorambucil (Sigma Chemical Co., USA) )1–2 mg diluted in 50 µl of DMSO immediately before use), cisplatinum (in saline solution) (David Bull Laboratories, Australia), vinblasine (Sigma Chemical Co., USA), solasodine glycosides, 100 mg in 5 ml DMSO and diluted to give a 5% solution of DMSO. Appropriate DMSO cytotoxicity studies were also conducted. Solasodine glycosides were supplied as a mixture (BEC), and as separate components, solamargine, solasonine, a mixture of di- and mono-glycosides and the aglycone solasodine. All cytotoxic drugs were further diluted with HIFCS/TCM before testing. $5\times10^4$ ovarian cancer cells (200 µl/chamber of a chamber of microscope slide (Lab Tek Miles Scientific) were used. Controls received 50 µl HIFCS/TCM and experimental chambers 50 µl of solasodine glycosides (BEC) 1.5–3.8 µM/L after 7 hrs preincubation, and incubated for a further 3 hrs. Similarly, the cells were treated with the aglycone solasodine 19.4–96.8 µM/L. The cells were fixed and examined by the Papanicolaou method.

Solasonine at 11.3 µM/L was ineffective in inhibiting the uptake of tritiated thymidine by the various cell types relative to solamargine at 11.5 µM/L (Table 1). The mixture of di- and mono-glycosides at 14.45 µM/L were also ineffective for lymphoblasoid cells and HeLa cells, whereas they caused approximately 30% inhibition for ovarian cancer cells and fibroblasts (Table 1). The highest concentration of BEC used contained 6 µM/L of di- and mono-glycosides and this would account for 10%–12% inhibition for susceptible cells. In order that comparisons could be made with previous studies, and because of the limited availability of the individual glycosides, the mixture of solasodine glycosides BEC was used for further investigations and the molar concentration expressed in terms of the most cytotoxic component solamargine.

In contrast to the other cells that have been investigated, solamargine has limited cytotoxicity for unstimulated lymphocytes and lymphocytes stimulated with Con A, and an absence of cytotoxicity when lymphocytes are stimulated with PHA or PWM (Table 2). Solasonine was also found to be ineffective (Table 2). The composition BEC has been used in this investigation and the cytotoxicity of BEC expressed in terms of the most active components, in this case, the di- and mono-glycosides (DMG).

From the dose response curves (FIGA. 1a,b,c,d), the lethal dose (LD) of cytotoxics required to inhibit 50% ($LD_{50}$) uptake of tritiated thymidine was determined. The $LD_{50}$ of the various cell types can be expressed as a ratio relative to the $LD_{50}$ of ovarian cancer cells, to give a thymidine uptake ratio ($TR_{50}$). Therefore, $TR_{50}$ values greater than 1.0 indicate that more ovarian cancer cells are killed relative to the other cell type (Table 3). From Table 3, other $TR_{50}$ can be calculated. The $TR_{50}$ for fibroblasts/lymphoblastoid cells in the presence of vinblastine is 0.73, which demonstrates its known cytoxicity to normal cells. Similarly, the $TR_{50}$ for chlorambucil (alkylating) and cis-platinum (DNA binding) which are used in the treatment of chronic lymphatic leukemia (CLL) and ovarian cancer respectively, also reflects their known attendant toxicity, although that of chlorambucil is not reflected by fibroblasts.

However, in the case of vinblastine or cis-platinum, the low $TR_{50}$ for fibroblasts relative to ovarian cancer cells is evident (Table 3). In contrast, solamargine gives a $TR_{50}$ greater than 2 for fibroblasts and lymphoblastoid cells relative to ovarian cancer cells. This suggests that solamargine has an acceptable degree of specificity for ovarian cancer cells, and under these conditions is superior to the other cytotoxic drugs. The specificity of solamargine for ovarian cancer cells is also reflected by the $TR_{50}$ relative to HeLa cells (Table 3). In addition, the molar concentration of solamargine that is required to achieve an $LD_{50}$ for ovarian cancer cells is 6–40 times less than that of the other cytotoxics investigated (Table 3).

Figure 8A:
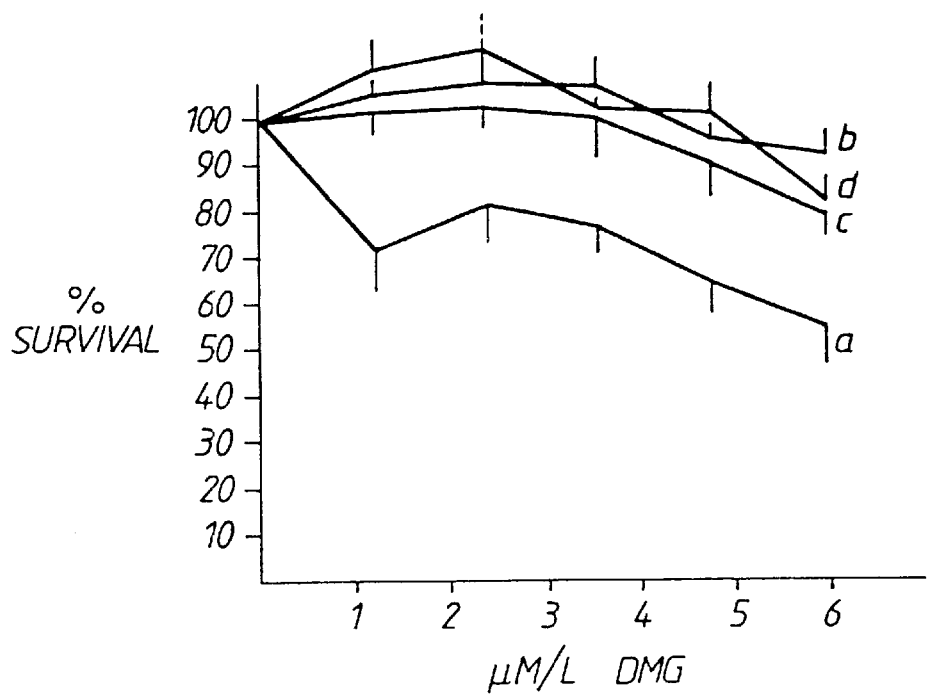
FIGS. 8a, 8b, 8c, 8d, and 8e, respectively, are graphs showing the cytotoxic effect of glycosides on lymphocytes.
Figure 8B:
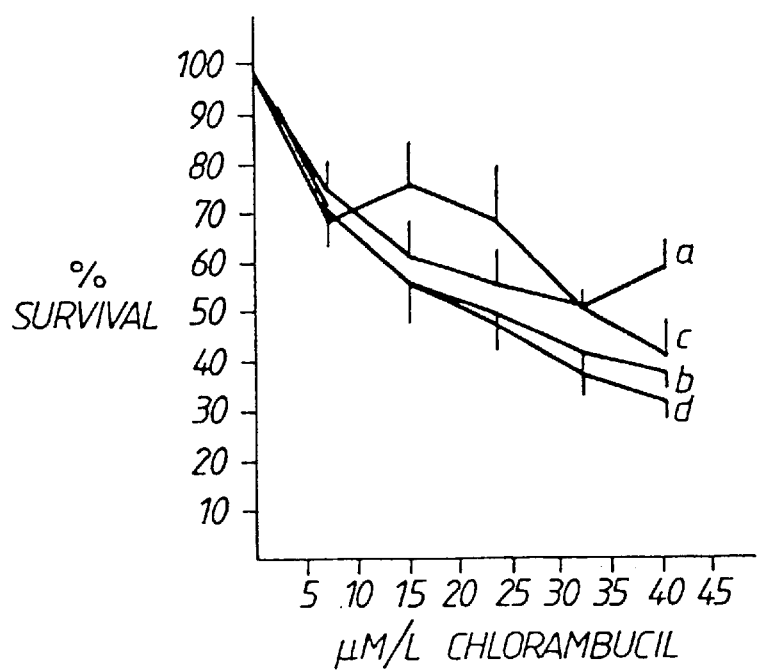
Figure 8C:
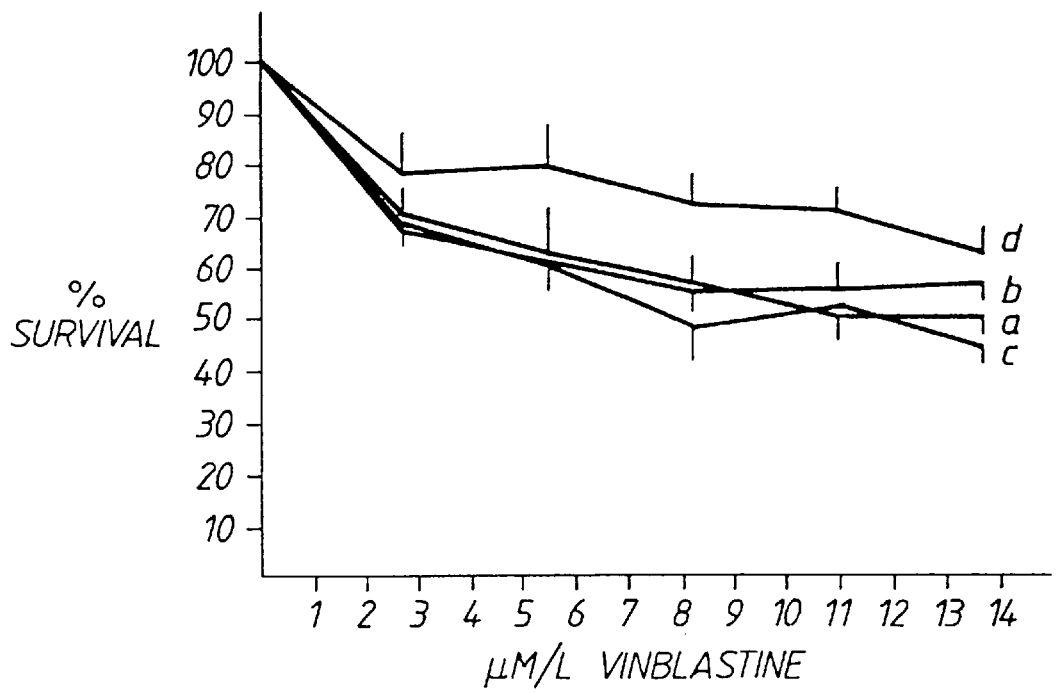
Figure 8D:
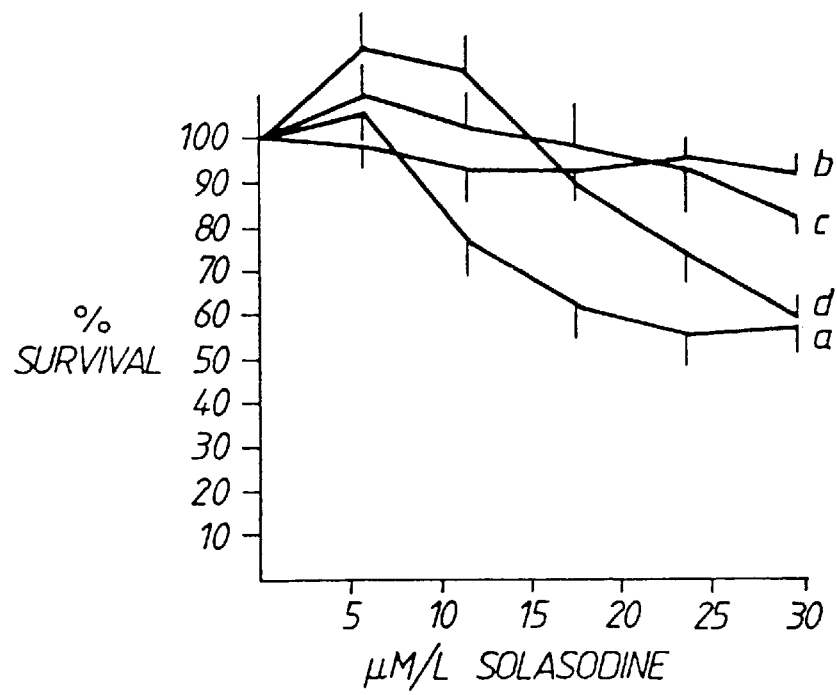

The $LD_{50}$ from the dose response curves (FIGS. 8a,b,c,d) for lymphocytes have been calculated and are presented in Table 4. The $LD_{50}$ for DMG indicates that they are equivalent or more cytotoxic than the other anti-neoplastic drugs investigated except in the case of PWM stimulated lymphocytes. The $LD_{50}$ concentration for the di- and mono-glycosides of solasodine (DMG) is increased with stimulated lymphocytes, in particular with PWM stimulation. Stimulated lymphocytes undergo a number of changes, which includes and increase in plasma membrane permeability, and this may account for the variable $LD_{50}$ for some of the cytotoxic drugs investigated. However, this situation does not appear to apply to DMG. Firstly, PHA and PWM stimulation of lymphocytes negates, rather than enhances the effect of DMG. Similarly, this applies to the effect of solamargine and the absence of any effect of solasonine on unstimulated and stimulated lymphocytes (Table 2). Secondly, the only difference between the glycosides are their carbohydrate moieties (glycone), because they all contain the same aglycone solasodine. This suggests that the different effects of the glycosides on unstimulated lymphocytes are due to the presence or absence of different EELs.

Cellular Uptake by Endocytic Endogenous Lectins

A mixture of solasodine glycosides (BEC), of which the active compound is solamargine and from which the aglycone solasodine is derived was prepared for use in cytotoxicity assays as determined by the uptake of tritiated thymidine. Inhibition studies were carried out with lactose, lactosyl-albumin, galactose or rhamnose (Sigma Chemical Co., USA). All experimental replicates were related to their own controls. Total volume of replicates was 250 μl (carbohydrates added in 50 μl tissue culture media+10% fetal calf serum), and the cell concentrations were $8\times10^4$/ml.

A human ovarian cancer cell line (C180–135) was grown as mono layers and trypsinized to form a cell suspension. The cells were adjusted to a concentration of $1\times10^5$/ml (viability ≧95%) and 200 μl placed in each of the eight chambers of microscope chamber slides (Lab Tek, Miles Scientific). After 21 hours preincubation at 37.5° C., 50 μl of supplemented tissue culture media were added to the control chambers. To the other chambers were added 50 μl of solasodine glycosides (BEC) to give final concentrations of 3, 4.8, 6.7, 7.7, 9.6, 11.1 and 15.3 μM/L. Similarly, to a separate chamber slide was added the aglycone solasodine (19.4–96.8 μM/L). The slides were incubated at 37.5° C. for a further 3 hours, and the cells fixed in 95% V/V alcohol and stained by the Papanicolaou method. Two other chamber slides were prepared in a similar manner, but the solasodine glycosides and the aglycone were added at a final concentration of 0.77, 1.5, 2.3, 3.1 and 3.8 μM/L after 7 hours preincubation, and they incubated for a further 17 hours.

As the ovarian cells (CI80–135) are more susceptible to the cytotoxic effects of solamargine in the BEC mixture of solasodine glycosides, these cells were selected as a representative example of the response of susceptible cells. Lysosomotropic drugs are weakly basic amines, like solamargine, which can be trapped and accumulate as the protanated (acidic) form in the lysosomes. This results in the rupture of the lysosomal membranes and the release of their proteolytic enzymes.

In order to observe any immobilization of spermatozoa, sperm ($10\times10^6$/ml) (50 μl) were placed on a microscope slide separated from 50 μl of solamargine (1 mg/ml) by 5 μl of eosin. A cover slip was then placed over the slide. The drops spread out but do not mix with each other to any great extent. This is a standard method known in the art. It was noted that sperm was not present on the side of the slide where the drop of solasodine glycosides was placed.

Figure 5:
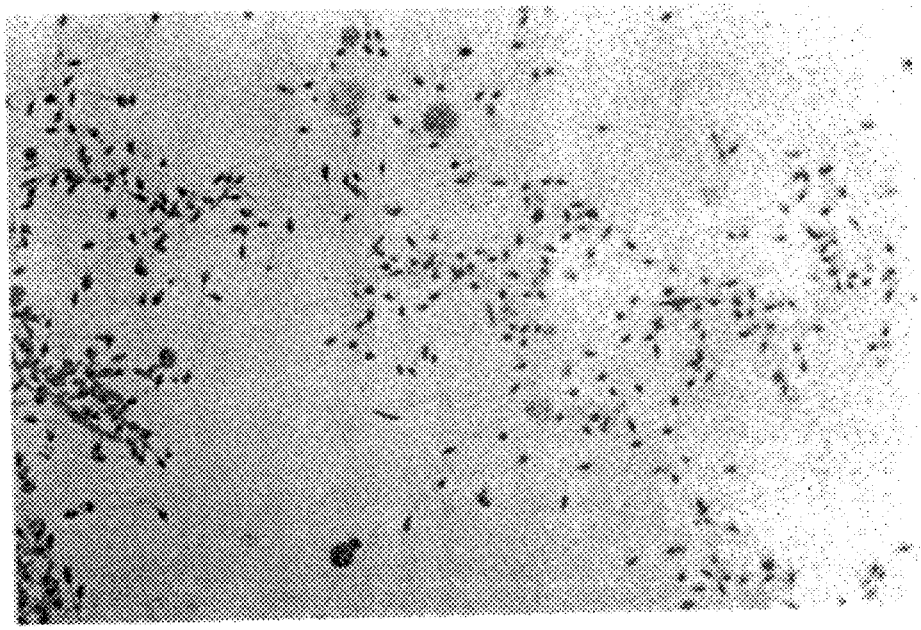
FIG. 5 is a microscopic photograph of dead intact spermatozoa in the zone of solamargine/eosin.
Figure 6:
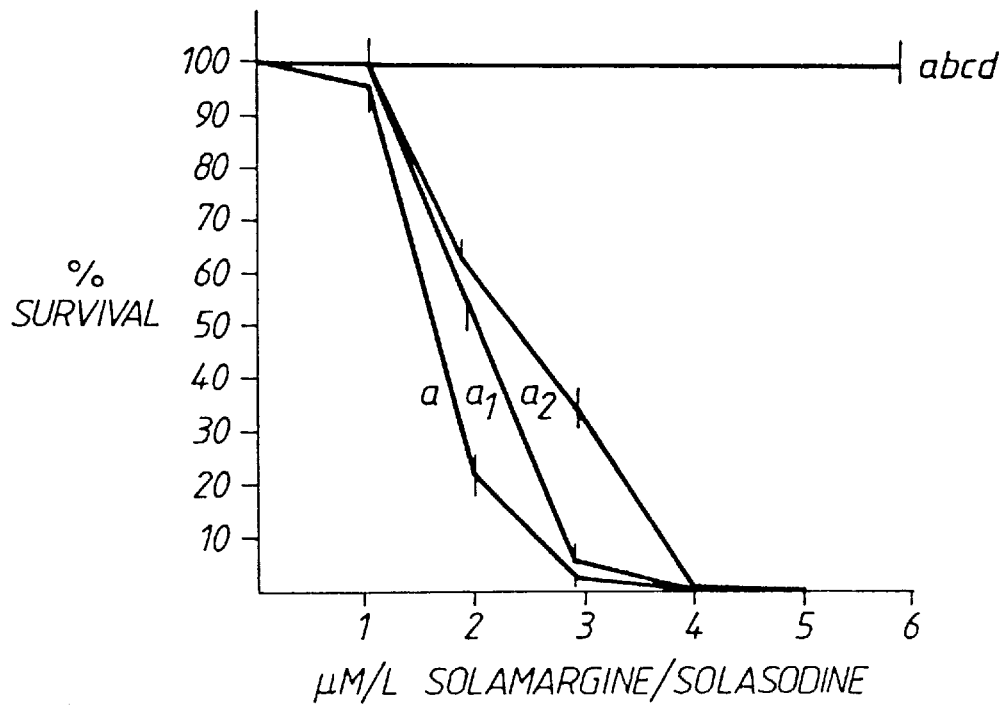
FIG. 6 is a graphic representation of the cytotoxic effect of aglycone solasodine at equivalent concentrations of solamargine.
Figure 7:
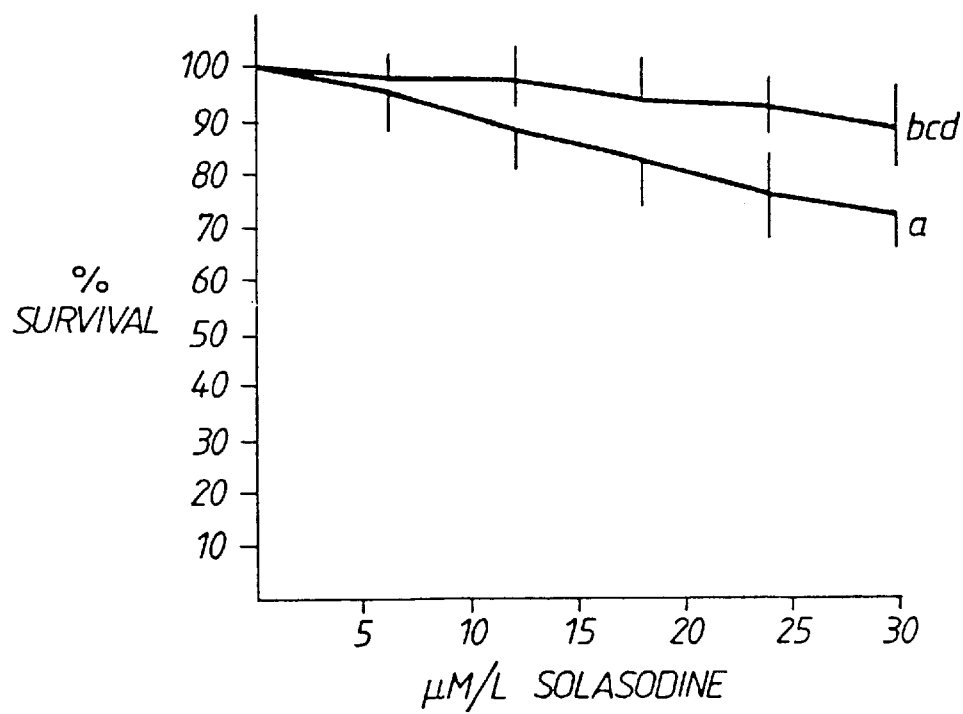
FIG. 7 is a graphic representation of the cytotoxic effect of solasodine at higher concentrations.

The results are presented in Tables 5 and 7 FIGS. 5, 6 and 7. The legend for FIGS. 6 and 7 is as follows:

a=ovarian cancer cells (FIG. 6 and FIG. 7)

$a_1$=ovarian cancer cells in the presence of lactose 1.1 μM/L (FIG. 6).

$a_2$=ovarian cancer cells in the presence of lactosyl-albumin 1.1 μM/L lactose (FIG. 6).

bcd=HeLa cells, lymphoblastoid cells and fibroblasts respectively (FIG. 6 and FIG. 7).

FIG. 6: Top curve—effect of the aglycone solasodine.

Partial inhibition of solamargine cytotoxicity by lactose and lactosyl-albumin is demonstrable for ovarian cancer cells (FIG. 6). The lactosyl-albumin inhibitory effect is approximately 4 times that of lactose at equivalent lactose concentration (FIG. 6). This is because glycoconjugates have an increased affinity for their corresponding lectin relative to unconjugated carbohydrates. Similarly, lactose and galactose cause partial inhibition of solamargine cytotoxicity for both ovarian cancer cells and lymphoblastoid cells (Table 5). In contrast, lactose and galactose completely inhibit solamargine cytotoxicity in the case of fibroblasts, and inhibition by rhamnose is also demonstrable (Table 5). Rhamnose is not found in mammalian glycoconjugates, but under certain conditions, can be identified by galactose reactive lectins. Therefore, the EEL expressed by cells susceptible to solamargine has specificity for Gal(1→4)Glu (2→1)Gal. It is therefore possible that lactose may compete for this EEL, in terms of the lactose group (Gal(1→4)Glu) and galactose/rhamnose for the terminal galactose ((2→1) Gal).

Similarly, these carbohydrate moieties of solamargine may be identified by their corresponding EEL's. This latter situation appears to apply to fibroblasts, as solamargine cytotoxicity was completely inhibited by lactose and galactose (Table 5). However, in the case of HeLa cells, solamargine cytotoxicity is not inhibited by lactose and galactose. Further, solasonine, a glycoside of solasodine, with a glycone moiety Glu(1→3)Gal(2→1)Rh is not cytotoxic. This gives further support for the presence of an EEL specific for Gal(1→4)Glu(2→1)GAl. Whether or not the partial inhibition of solamargine cytotoxicity by lactose and galactose, in the case of ovarian cancer cells and lymphoblastoid cells (Table 5), is the result of competitive inhibition or the presence of lactose and galactose EELs, has not been elucidated.

The aglycone solasodine does not exert a cytotoxic effect at equivalent concentrations of solamargine (FIG. 6). However, at higher concentrations, there is an increase in cytotoxicity, but this is more apparent with ovarian cancer cells (FIG. 7). This may be explained by the changes in membrane permeability of cancer cells. It is possible that solasodine, which is a very hydrophobic molecule, undergoes enhanced protein-binding and thus reduces its bioavailability. Cytotoxic effects therefore become apparent at higher concentrations. Nevertheless, collectively, the results demonstrate the presence of EELs for solamargine.

Figure 8E:
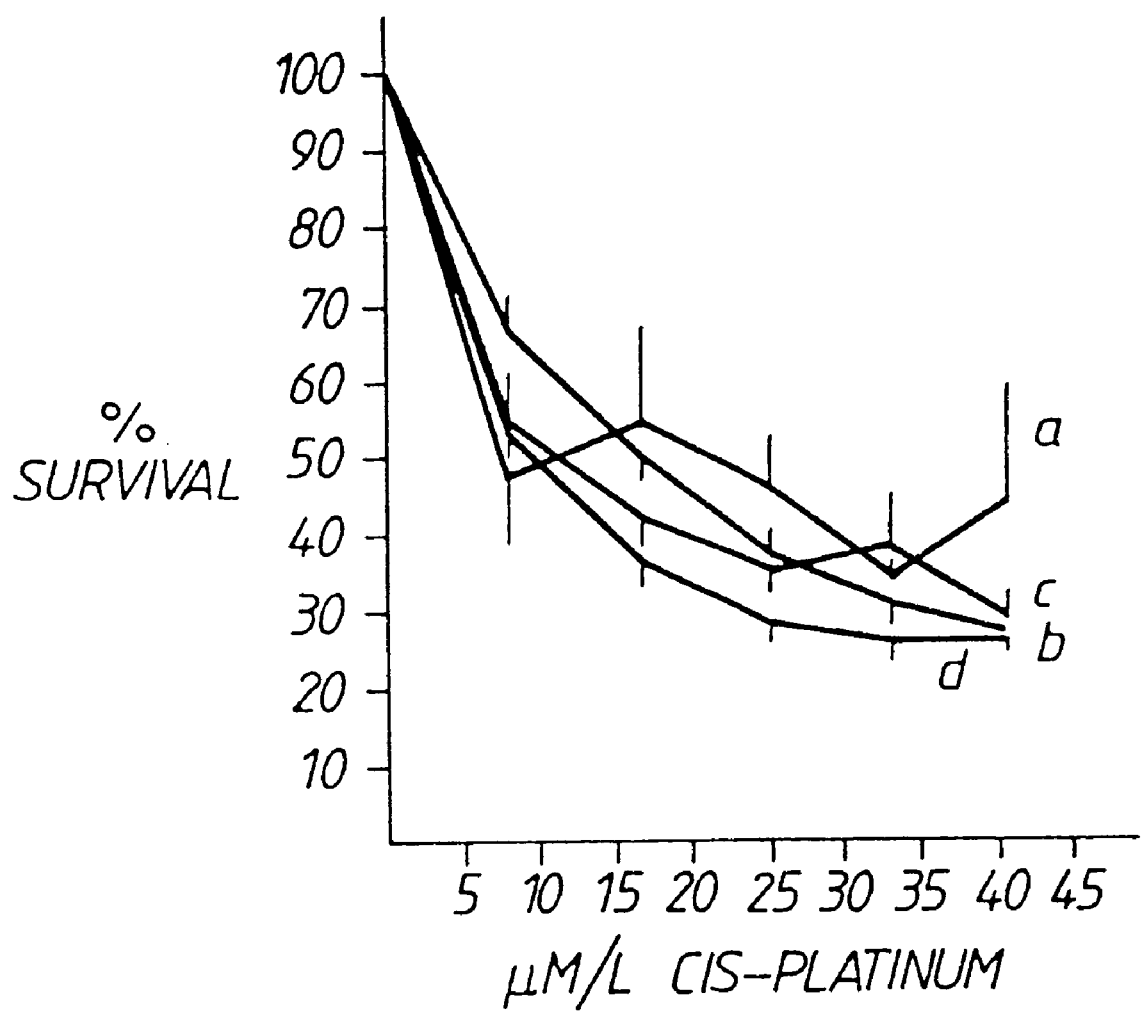

The aglycone solasodine does not exert a cytotoxic effect at equivalent concentrations of DMG. However, at much higher concentrations, there is a substantial effect on unstimulated lymphocytes, which is significantly reduced in the case of stimulated lymphocytes (FIG. 8e). This suggests that membrane permeability to the aglycone is decreased in stimulated lymphocytes. However, this would not account for the differential effect of the glycosides on unstimulated and stimulated lymphocytes (Table 2, FIGS. 8a,b,c,d), and inhibition by carbohydrates (Table 7). Thus, collectively the results support the active uptake of solasodine glycosides by EELS.

Glucose or rhamnose inhibit the action of DMG with Con A stimulated lymphocytes (Table 7). Since these carbohydrates do not inhibit DMG with unstimulated lymphocytes, this suggests that Con A stimulation results in the expression of EELs that react with glucose and rhamnose. Thirdly, Con A stimulation gives rise to a subpopulation of T suppressor cells (TS) that inhibit helper T cells (TH) within the total population. The TS cells produce soluble factors that inhibit TH cell functions but these suppressor factors can be inhibited by N-acetylglucosamine or rhamnose by completing the TH cell receptors. Therefore, one of the soluble TS cell factors and/or Con A may be involved in receptor (EEL) induction on TH cells.

The aglycone solasodine did not have any observable effect on the ovarian cancer cells at any of the concentrations investigated (FIG. 2A). In contrast, with increasing concentration of the solasodine glycosides (expressed as concentration of solamargine) over 3 hours, the cytoplasm of the cancer cells undergo dissolution, the nuclei contract and become dark staining (FIG. 2B), nuclei then enlarge (FIG. 3A), the chromatin clumps (FIG. 3B), and finally the nuclei disintegrate (FIG. 4A). FIG. 4B represents the effect of the solasodine glycosides over 17 hours, in which cellular debris is left. It therefore appears that the inhibition of thymidine uptake by solamargine is the result of cell lysis.

Solamargine was also found to inhibit human spermatozoal motility (FIG. 5) as a red line of demarcation between the sperm in tissue culture media and the solamargine aliquot became visible as sperm penetrated the boundary and then became immobilized within 15 sec.

The immobilization of spermatozoa can result from the inactivation of their mitochondria, and in the case of cells that contain lysosomes, this could lead to rupture of the lysomal membranes.

The preferential cancer cells cytotoxicity (lysosomotropic/mitochondrial inhibition) of solamargine appears to be effective against both proliferating and resting cancer cells, as evidenced by the absence of cancer cells upon cytological examination (FIG. 4B). In addition, the lack of lysosomotropic/mitochondrial inhibition by the aglycone solasodine, the triglycoside solanine and the di- and mono-glycosides of solasodine indicates that the cellular uptake of solamargine is possibly mediated by plasma membrane endocytic endogenous lectins (EELs), specific for the carbohydrate moiety of solamargine.

Fluorescence Activated Cell Sorter Analysis (FACS)

To verify the inhibition studies of the "free" sugars and sugars covalently bound to albumin (uptake of $^3$H-thymidine) were due to competition for endogenous lectin receptors, FACS analysis was used. This involves the use of sugar(s) covalently bound to bovine serum albumin and the fluorescent compound FITC (S-Alb-FITC). To $1\times10^6$ cells, washed twice in phosphate buffered saline pH 7.2 containing 10 mg/ml of bovine serum albumin, 1 mM $CaCl_2$ and 0.5 mM $MgCl_2$ was added 1.0 ml of SAlb-FITC 200 µg/ml in the same buffer and incubated for 1 hour. This experiment was conducted at two different temperatures, 4° C. and ambient temperature (RT). At 4° C. the endogenous lectins would undergo endocytosis (internalization by the cells) at a slower rate when complexed to S-Alb-FITC relative to that at RT. Thus a greater percentage of fluorescence should be expressed at RT, unless the cells were expressing excessive amounts of endogenous lectins.

The data for the lactose specific lectin receptor is presented in Table 6 for a number of cell types.

Inhibition of Cytotoxicity by Rhamnose in Mice with Sarcoma 180

Rhamnose is not found in mammalian glycoconjugates but forms part of solasonine, solamargine and diglycosides of solasodine in BEC. If specific receptors for this sugar are present on cancer cells (absolutely or in greater abundance) relative to normal cells, then rhamnose would be expected to inhibit the cytotoxic effects of BEC.

Below it is shown that rhamnose inhibits the efficacy of BEC, and that the aglycone solasodine is not effective against murine S180. It is also demonstrated that mice in their terminal stage with S180 can tolerate and become symptom-free of cancer by a large single dose of BEC. The mice tolerate BEC at concentrations which are equivalent to 3 times the $LD_{100}$ of control normal mice.

Herston White mice with a body weight of approximately 30 g and aged 8–10 weeks served as recipients. Twelve mice were randomly chosen for each experimental group.

Sarcoma 180 tumour cells ($5\times10^5$) were inoculated intraperitoneally into mice. This caused a mortality of 100% with a median survival time of 20 days in the control groups. A standard mixture of glycoalkaloids (BEC) was dissolved in dimethylsulfoxide at a concentration of 0.5 g BEC/100 ml dimethylsulfoxide. Similar solutions were made up but also contained 0.3125, 0.625 and 0.9375 g of rhamnose. These solutions were administered intraperitoneally in concentrations of 8 mg/kg animal weight for BEC (FIG. 9) without (-▲-), and with 5 mg (-□-), 10 mg (-•-) and 15 mg (-Δ-) rhamnose/kg animal weight. The first dose was given 0.5 hours after administration of the Sarcoma 180 tumour cells. The remaining three doses were given at daily intervals. Dimethylsulfoxide and rhamnose had no effect on Sarcoma 180 activity in the absence of BEC (-o-).

Figure 9:
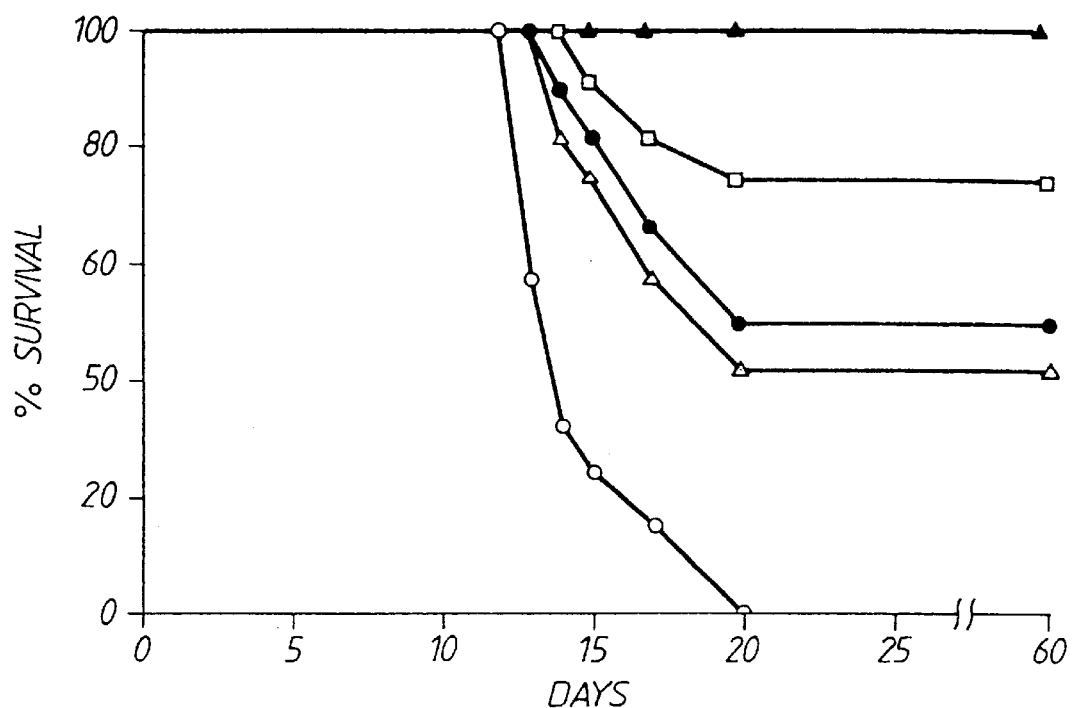
FIG. 9 is a graphic representation of the survival rate of mice treated with compounds in accordance with the present invention.

Using similar conditions to those described in FIG. 9, single high doses of BEC (FIG. 10) 25 mg/kg (-o-), 50 mg/kg (-▼-), and 100 mg/kg (-■-) were administered intraperitoneally 12 days after inoculation of the Sarcoma 180 tumour cells (arrow), that is, one day before the animals enter into the terminal stage. Dimethylsuphoxide had no effect on Sarcoma 180 activity and all animals died in 20 days (-•-).

FIG. 9 illustrates that the survival of mice with S180 treated with 4 doses of 8 mg BEC/kg was dependent on given doses of rhamnose. Mice inoculated with S180 cells alone died in 2–3 weeks. When four doses of BEC at 8 mg/kg were given on consecutive days, complete inhibition of S180 activity was achieved and all the animals survived. The number of survivals was decreased with increasing concentrations of rhamnose. Five mg rhamnose/kg decreased the survival to 75%, whereas 10 mg rhamnose/kg decreased the survival to 50% and 15 mg rhamnose/kg decreased the survival to 42%. This indicates that rhamnose may competitively inhibit the efficacy of BEC. Similar concentrations of rhamnose or glucose have no effects on S180 activity in the absence of BEC. These observations suggest that the binding of solasodine glycosides on tumour cells may be mediated through the monosaccharide rhamnose, which forms part of solasonine, solamargine and diglycosides of solasodine in BEC.

Figure 10:
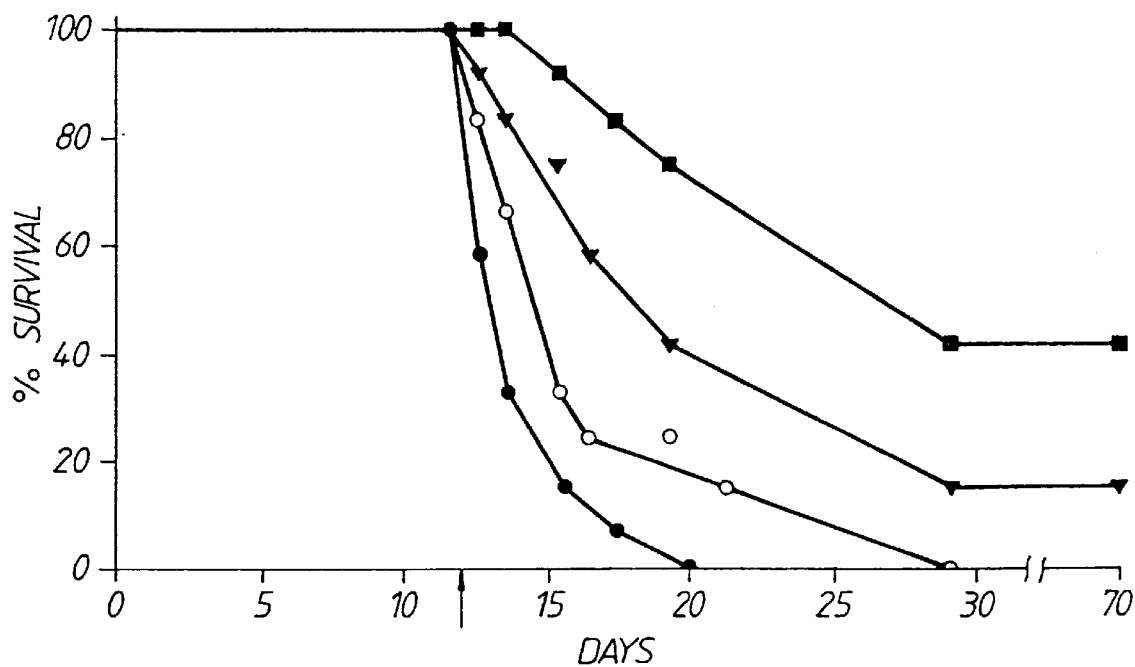
FIG. 10 is another graphic representation of the survival rate of mice treated with compounds in accordance with the present invention.

In all reported in vivo studies with S180, BEC was injected before the terminal phase. FIG. 10 illustrates the effect of single doses of varying concentrations of BEC on the absolute survival of mice which had the S180 tumour for 12 days, that is, one day before the animals enter into the terminal stage. All animals inoculated with S180 and not treated with BEC died. The survival time is increased with a dose of 25 mg/kg. However, at day 30, all the mice had died. The survival time and number of survivors were increased with increasing concentrations of BEC, and 17% were symptom-free with a given dose of 50 mg/kg, whereas 42% were symptom-free with a given dose of 100 mg/kg.

There are two important observations to note from these results.

The first is that animals which are in their terminal stage can be rendered symptom-free of S180 by BEC therapy.

The second is that the animals can tolerate very high doses of BEC. It is known that the $LD_{50}$ (intraperitoneal) of BEC in mice is 30 mg/kg for single doses and the $LD_{100}$ is 35 mg/kg. Thus, in the present studies, it is shown that if the mice suffered from advanced S180 activity, virtually three times the $LD_{100}$ of BEC for normal mice can be tolerated. This important observation has not been reported with other antineoplastic drugs.

This lack of toxicity may be due to increased plasma or tissue enzymatic activity, resulting in hydrolysis of the sugars from the solasodine. Solasodine is relatively non-toxic in mice (100 mg solasodine/kg—which is equivalent to approximately 200 mg BEC/kg—does not produce any deaths in mice). However, this is unlikely, since solasodine at similar concentrations (100 mg/kg) is not effective in inhibiting S180 activity in mice, and FIG. 10 shows clearly that S180 activity was inhibited by the equivalent concentration of BEC. Alternatively, and a more likely explanation, is that the S180 cells which are in great abundance in the ascitic fluid of the mice 12 days after inoculation of S180 cells, recognize and bind BEC by means of specific receptors (endogenous lectins), reducing the bioavailability of BEC to normal cells, which in turn reduces the toxicity of BEC. Furthermore, this explanation is supported by the fact that BEC inhibits S180 activity even though the animals are suffering from advanced S180 activity. At this advanced stage, BEC, at concentrations less than 25 mg/kg is not effective in inhibiting S180 activity. These results provide evidence that BEC selectively destroys tumour cells relative to normal cells and the mode of entry of BEC into tumour cells appears to be mediated by the sugar moiety of the solasodine glycosides.

TABLE 1

Percentage Cell Survival in the Presence of Solasodine Glycosides

| | Percentage Survival: Cell Type | | | |
|---|---|---|---|---|
| | OvCa | HeLa | LCL | FB |
| BEC 12.42 μM/L | 0.6 ± 0.1 | 27 ± 7 | 54 ± 4 | 48 ± 6 |
| Solamargine 11.5 μM/L | 7 ± 0.8 | 2.6 ± 0.5 | 35 ± 4.2 | 23 ± 1.7 |

TABLE 1-continued

Percentage Cell Survival in the Presence of Solasodine Glycosides

| | Percentage Survival: Cell Type | | | |
|---|---|---|---|---|
| | OvCa | HeLa | LCL | FB |
| Solasonine 11.3 μM/L | 93 ± 8.0 | 105 ± 9.5 | 117 ± 8.0 | 96 ± 8.3 |
| di- & mono-glycosides 14.45 μM/L | 71 ± 9.0 | 94 ± 8.3 | 97 ± 11.0 | 76 ± 5.7 |

OvCa = ovarian cancer cells;
HeLa = HeLa cells;
LCL = lymphoblastoid cells;
FB = fibroblasts.

TABLE 2

Percentage Survival of Unstimulated and Stimulated Lymphocytes in the Presence of Solasodine Glycosides

| | Percentage Survival | | | |
|---|---|---|---|---|
| S.G. | US | PHA | Con A | PWM |
| BEC 12.42 μM/L | 63 ± 7 | 95 ± 4 | 90 ± 8 | 100 ± 7.5 |
| Solam 11.5 μM/L | 76 ± 9.6 | 93 ± 4.4 | 79 ± 4 | 93 ± 9.4 |
| Solas 11.3 μM/L | 97 ± 11.8 | 103 ± 5.7 | 97 ± 7 | 110 ± 3.8 |
| DMG 14.45 μM/L | 40 ± 4.6 | 93 ± 4.2 | 57 ± 5 | 103 ± 9.7 | n = 10

SG = solasodine glycosides
BEC = Solam, Solas and DMG
Solam = Solamargine
Solas = solasonine
DMG = di- and mono-glycosides
US = unstimulated lymphocytes
PHA, Con A and PWM = stimulated lymphocytes

TABLE 3

Dose of Cytotoxic (μM/L) to Inhibit 50% Tritiated Thymidine Uptake $LD_{50}$) and Expressed as Thymidine Ratio ($TR_{50}$) Relative to Ovarian Cancer Cells

| Cytot | OvCa | HeLa | TR | LCL | $TR_{50}$ | FB | $TR_{50}$ |
|---|---|---|---|---|---|---|---|
| Solam | 1.55 μM/L | 2.5 μM/L | 1.6 | 3.95 μM/L | 2.5 | 3.65 μM/L | 2.3 |
| V.B. | 9.5 μM/L | 2.7 μM/L | 0.28 | 2.6 μM/L | 0.27 | 1.9 μM/L | 0.2 |
| C.P. | 63 μM/L | 49.5 μM/L | 0.78 | 50 μM/L | 0.79 | 95.5* μM/L | 1.5 |
| CB | 60 μM/L | 47.5 μM/L | 0.79 | 27 μM/L | 0.45 | NSE μM/L | — |

Cytot = cytotoxic;
V.B. = vinblastine;
CB = chlorambucil;
HeLa = HeLa cells;
FB = fibroblasts
* = extrapolation;
NSE = no significant effect
Solam = solamargine;
C.P. = cis-platinum;
OvCa = ovarian cancer cells;
LCL = lymphoblastoid cells

TABLE 4

LD$_{50}$ Concentration of Cytotoxic Drugs for
Unstimulated and Stimulated Lymphocytes

|     | CB μM/L | CP μM/L | VB μM/L | DMG μM/L |
|-----|---------|---------|---------|----------|
| US  | 33.0    | 21.0    | 11.0    | 6.4      |
| PHA | 24.6    | 17.0    | 19.2⁻   | 14.8*    |
| Con A | 33.0  | 11.0    | 7.8⁻⁻   | 11.2**   |
| PWM | 22.0    | 9.0     | 10.8⁻⁻  | 196.0*** |

Figure 1C:
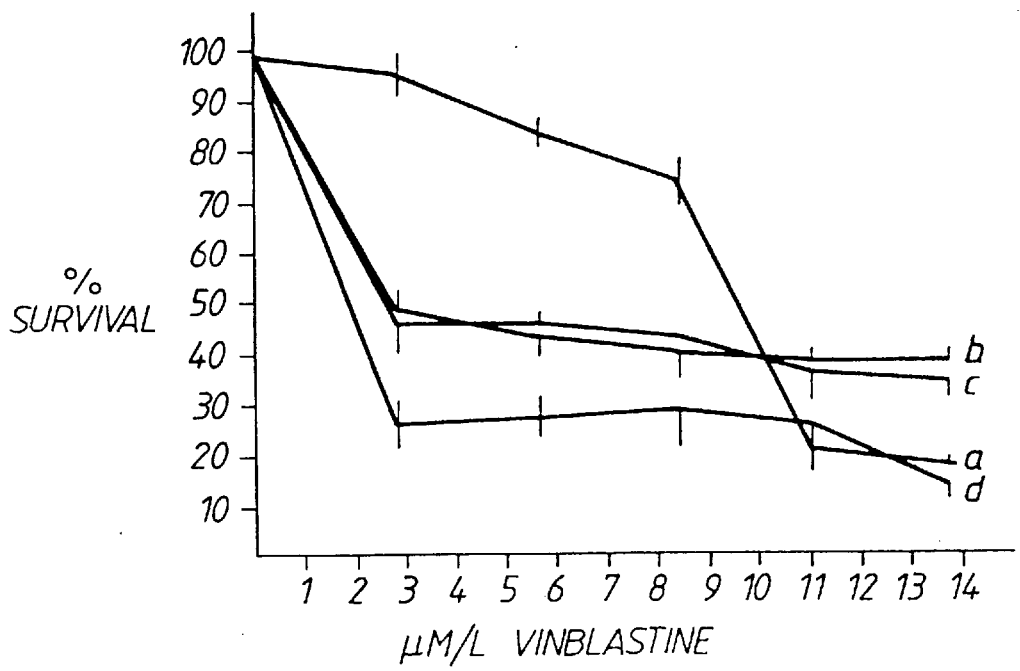
Figure 1D:
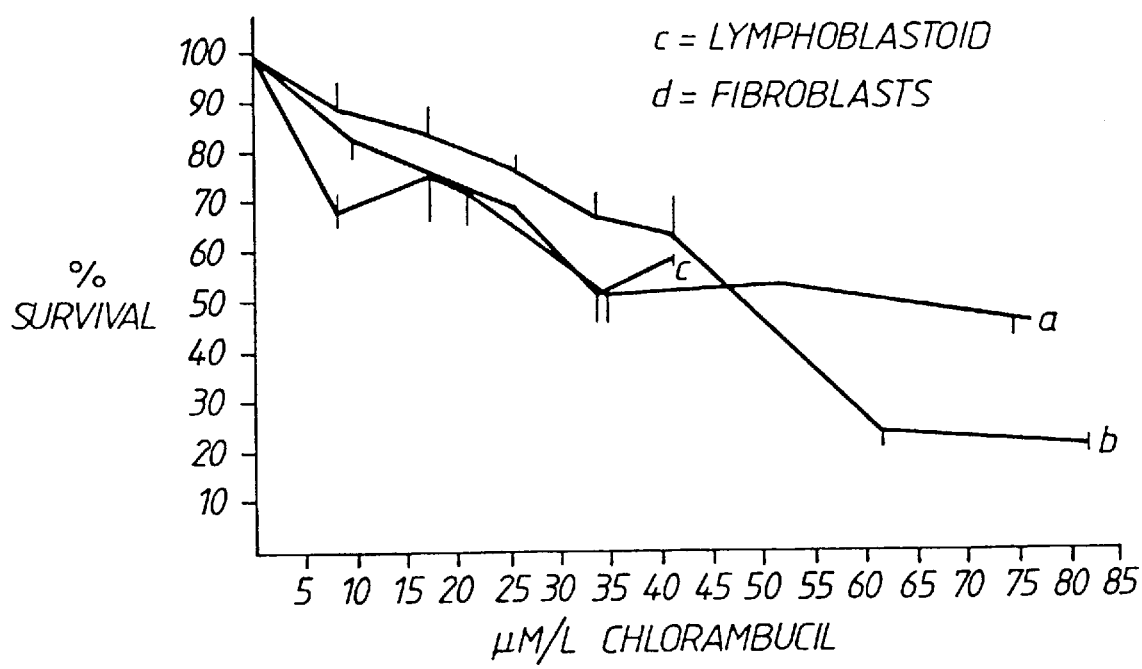

US = unstimulated lymphocytes
PHA, Con A and PWM = stimulated lymphocytes
CB = chlorambucil
CP = cis-platinum
VB vinblastine
DMG = di and mono-glycosides of solasodine
*extrapolation r = −0.86 p <0.05 >0.02 (from FIG. 1a)
**extrapolation r = −0.91 p = 0.01 (from FIG. 1a)
***extrapolation r = −0.89 p = <0.02 >0.01 (from FIG. 1a)
⁻extrapolation r = −0.811 p = 0.05 (from FIG. 1c)
⁻⁻extrapolation r = −0.94 p = <0.01 >0.001 (from FIG. 1c)

TABLE 5

Effect of Solamargine: Percentage Cell Survival in the Presence
and Absence of Lactose, Galactose or Rhamnose

| Cells | Solamargine Concn. | No Carbohydrate | 1.1 μM/L Lactose | 1.1 μM/L Galactose | 1.1 μM/L Rhamnose |
|-------|--------------------|-----------------|------------------|--------------------|--------------------|
| OvCa  | 1.54 μM/L          | 62 ± 7(9)       | 75 ± *11(7)      | 79 ± **10(10)      | 67 ± 7.5(9)        |
| HeLa  | 2.4 μM/L           | 25 ± 2.6(8)     | 24 ± 2.9(10)     | 24 ± 2.2(10)       |                    |
|       |                    | 24 ± 4(8)       |                  |                    | 26 ± 2.1(7)        |
| LCL   | 3.1 μM/L           | 34 ± 3(10)      | 47*** ± 4.8(10)  | 42*** ± 3(10)      | 36 ± 4.5(10)       |
| Fb    | 3.1 μM/L           | 58 ± 9.6(7)     | 100* ± 11(7)   | 101* ± 10(10)    | 87*** ± 6.7(10)    | n = 10

OvCa = Ovarian cancer cell line
HeLa = HeLa cells
LCL = Lymphoblastoid cells
Fb = Fibroblasts
Significant inhibition of solamargine
* = p < 0.02 > 0.01
** = p = 0.001
*** = p < 0.001

TABLE 6

FACS analysis of percentage of cells with lactose lectin receptors

| CELL TYPE | 4° C. | RT |
|-----------|-------|-----|
| Viral infected cells | 49% | 55% |
| Ovarian cancer cells | 67% | 83% |
| Fibroblasts | 29% | 33% |
| Lymphocytes | 27% | 43% |
| Lymphocytes stimulated | 52% | 72% |

TABLE 7

Percentage Survival of Unstimulated and Con A Stimulated
Lymphocytes in the Presence of Solasodine Glycosides
and Carbohydrates

| | DMG Conc. | | 1.1 μM/L Lactose | 1.1 μM/L Galactose | 1.1 μM/L Glucose | 1.1 μM/L Rhamnose |
|---|---|---|---|---|---|---|
| US | 4.81 μM/L | 72 ± 12 | 69 ± 12 | 77 ± 8.6 | 76 ± 15 | 85 ± 12 |
| Con A | 4.81 μM/L | 85 ± 11 | 75 ± 5.5 | 84 ± 11.8 | 109 ± 15* | 102 ± 11** | n = 7

* p < 0.01 > 0.001
** p < 0.02 > 0.01
DMG = di- and mono-glycosides
US = unstimulated, Con A = stimulated It has been demonstrated that alkaloids will induce cellular autophagy (self-digestion) and/or cell agglutination or immobilization. These effects of such alkaloids are greatly enhanced when conjugated to certain ligands, particularly carbohydrates (glycoconjugates). The invention is particularly effective if the cell to be targeted possesses receptors that recognise a rhamnose—or a rhamnose-like—residue. By conjugating different ligands to these alkaloids, it is possible to induce autophagy and/or cell agglutination or immobilization of specific cell types.

The most cytotoxic compound is solamargine, the dose required to inhibit DNA synthesis by 50% ($LD_{50}$) of an ovarian cancer cell line and HeLa cells being 1.5–3.3 times less than that required for lymphoblastoid cells and fibroblasts. The effective $LD_{50}$ of solamargine is 6–40 times less than that of vinblastine, chlorambucil or cis-platinum, compounds that are equally or more cytotoxic to normal cells relative to cancer cells.

Although it is known that neoglycoprotein conjugates of cytotoxic drugs may be suitable for targeting of cells via EELS, this known art has only used mono- or disaccharide conjugates for this targeting of EELs which are also expressed by various normal cells.

Further, such prior art drugs are limited to the treatment of one type of malady and it is not possible to predict the effectiveness of such drugs in the treatment of a different type.

In contrast, the present invention demonstrates, inter alia, a more complex EEL on a ovarian cancer cell line and HeLa cells for the trisaccharide Gal(1 4)Glu(2 1)Gal, as well as EELs for lactose and galactose.

The presence of an EEL for a trisaccharide such as rhamnose is surprising as rhamnose is a plant sugar and is not generally known to occur in mammalian cells.

It is believed that the present inventors are the first to demonstrate that an EEL for a trisaccharide occurs on cancer cells relative to normal cells such that the difference in EEL expression can be exploited for increased specific targeting of cytotoxic glycoconjugates.

In this regard, given the lack of toxicity of solasodine glycosides relative to other cytotoxic drugs, the unique mode of action, the ability to be targeted via EELs and the potential to produce synthetic glycoconjugates of solasodine with enhanced specificity, the present invention should be of particular importance in cancer chemotherapy.

The present invention is expected to be of great value in the control of cellular function in all types of vertebrates or invertebrates, including bacteria, viruses, protozoa and fungi—for example, in the control of pathogenic organisms in blood, lymph and tissue; any new growth of tissue or tissue that is in an ectopic site; embryonic cells; non-malignant and malignant cells; spermatozoa and semen; ova; and for the control of biochemical manufacturing processes.

Further, it follows that the present invention can be used to prevent cell autophagy and/or cell agglutination or immobilization but change cellular metabolism—for example, the production of a tumour necrosis factor by cells, such as macrophages, and/or inhibition of cellular metabolism and catabolism.

It will be appreciated that the above experimental results are given by way of exemplification of the invention only and that changes may be made to the details set out therein without departing from the inventive concept as defined in the following claims.

We claim:

1. A method of immobilizing spermatozoa comprising contacting the spermatozoa with solamargine to cause immobilization of the contacted spermatozoa.

2. A method according to claim 1 wherein the solamargine is in a mixture of solasodine glycosides.

3. A method according to claim 1 wherein the solamargine is in a BEC mixture of solasodine glycosides.

4. A method of contraception comprising contacting the spermatozoa with solamargine to cause immobilization of the contacted spermatozoa.

5. A method according to claim 4 wherein the solamargine is in a mixture of solasodine glycosides.

6. A method according to claim 4 wherein the solamargine is in a BEC mixture of solasodine glycosides.

* * * * *